(12) United States Patent
Chen et al.

(10) Patent No.: US 6,818,773 B2
(45) Date of Patent: Nov. 16, 2004

(54) SYNTHESIS OF 4-[(Z)-4-BROMOPHENYL) (ETHOXYIMINO) METHYL]-1'-[(2,4-DIMETHYL-1-OXIDO-3-PYRIDINYL) CARBONY)]-4'-METHYL-1,4-'BIPIPERIDINE

(75) Inventors: Minzhang Chen, Plainsboro, NJ (US); Bosco Anthony D'Sa, Edison, NJ (US); William W. Leong, Westfield, NJ (US); Tong Gan, North Brunswick, NJ (US); George S. K. Wong, Summit, NJ (US); Suhan Tang, Edison, NJ (US); Christopher Michael Nielsen, Westfield, NJ (US)

(73) Assignee: Schering Corporation, Kenilworth, NJ (US)

(*) Notice: Subject to any disclaimer, the term of this patent is extended or adjusted under 35 U.S.C. 154(b) by 196 days.

(21) Appl. No.: 10/269,822

(22) Filed: Oct. 11, 2002

(65) Prior Publication Data
US 2003/0105131 A1 Jun. 5, 2003

Related U.S. Application Data
(60) Provisional application No. 60/329,566, filed on Oct. 15, 2001.

(51) Int. Cl.⁷ .................... C07D 401/14; C07D 401/00
(52) U.S. Cl. .................................. 546/187; 546/186
(58) Field of Search ..................... 546/187, 186

(56) References Cited

U.S. PATENT DOCUMENTS
6,387,930 B1    5/2002   Baroudy et al.

FOREIGN PATENT DOCUMENTS
WO       WO 00/66559       11/2000

OTHER PUBLICATIONS

Palani, A. et al.: "Discovery of 4-[(Z)-(4-Bromophenyl)-(ethoxyimino)methyl]-1'-[(2,4-dimethyl-3-pyridinyl)carbonyl]-4'-methyl-1,4'-bipiperidine N-Oxide (SCH 351125): An Orally Bioavailable Human CCR5 Antagonist for the Treatment of HIV Infection", *J. Med. Chem.* 44(21), 3339–3342 (2001).

Primary Examiner—Charanjit S. Aulakh
(74) Attorney, Agent, or Firm—Palaiyur S. Kalyanaraman

(57) ABSTRACT

In one embodiment, the present invention describes the synthesis of 4-[(Z)-(4-bromophenyl)(ethoxyimino)methyl]-1'-[(2,4-dimethyl-1-oxido-3-pyridinyl)carbonyl]-4'-methyl-1,4'-bipiperidine, and intermediates therefor from easily available starting materials by a simple route.

42 Claims, No Drawings

SYNTHESIS OF 4-[(Z)-4-BROMOPHENYL) (ETHOXYIMINO) METHYL]-1'-[(2,4-DIMETHYL-1-OXIDO-3-PYRIDINYL) CARBONY)]-4'-METHYL-1,4'-BIPIPERIDINE

FIELD OF THE INVENTION

This application claims priority from provisional application Ser. No. 60/329,566 filed Oct. 15, 2001, and discloses a novel process to synthesize 4-[(Z)-(4-bromophenyl)(ethoxyimino)methyl]-1'-[(2,4-dimethyl-1-oxido-3-pyridinyl)carbonyl]-4'-methyl-1,4'-bipiperidine, and intermediates therefor.

BACKGROUND OF THE INVENTION

4-[(Z)-(4-bromophenyl)(ethoxyimino)methyl]-1'-[(2,4-dimethyl-1-oxido-3-pyridinyl)carbonyl]-4'-methyl-1,4'-bipiperidine (formula I) is disclosed in U.S. patent application, Ser. No. 09/562,815 filed May 1, 2000, which is incorporated herein by reference.

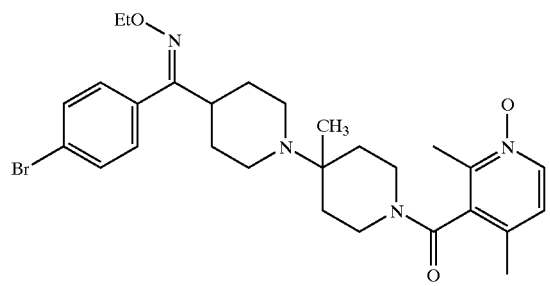

The compound of formula I is the base form of the compound of formula X which is an acid salt:

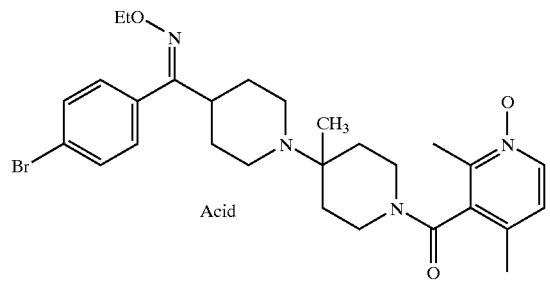

The compound of formula X is an antagonist of the CCR5 receptor and is useful for the treatment of AIDS and related HIV infections. CCR-5 receptors have also been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease. Patent application, Ser. No. 09/562,815 also teaches a method of making the compounds of formula I, and from I the compound of formula X.

In view of the importance of antagonists of the CCR5 receptor, new, novel methods of making such antagonists are always of interest.

SUMMARY OF THE INVENTION

In an embodiment, the present application teaches a novel, simple process of making a compound of formula I and, via that process, a method of making a compound of formula X if so desired. The compound of formula I is prepared from a compound of formula II:

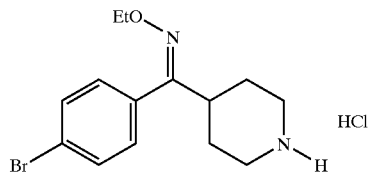

The process of making I from II comprises:

(a) converting the oxime of formula II to a compound of formula III:

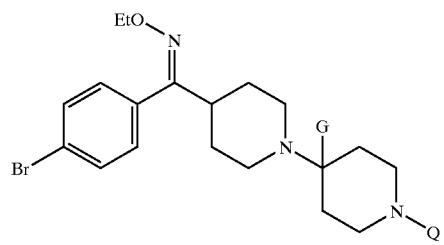

where G is a suitable leaving group selected from the group consisting of CN, Y, benzotriazolyl, $OSO_2R^1$ and $OCOCY_3$ with $R^1$ being an alkyl or aryl group and Y is a halogen (especially F or Cl); and Q is a suitable N-protecting group defined later;

(b) reacting said compound of formula III with a suitable Grignard reagent in a suitable solvent, followed by work-up, to yield a compound of formula IV:

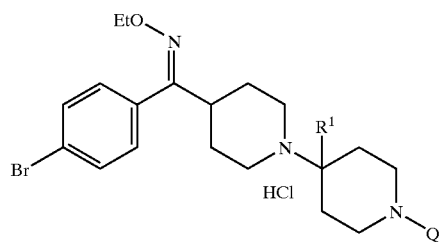

(c) deprotecting said compound of formula IV to a compound of formula V:

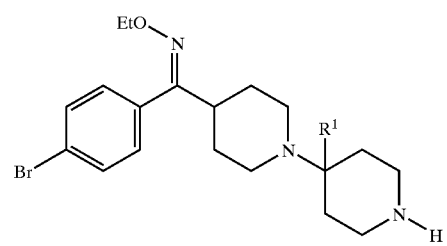

(d) forming the salt of the compound of formula V to form the compound of formula VI:

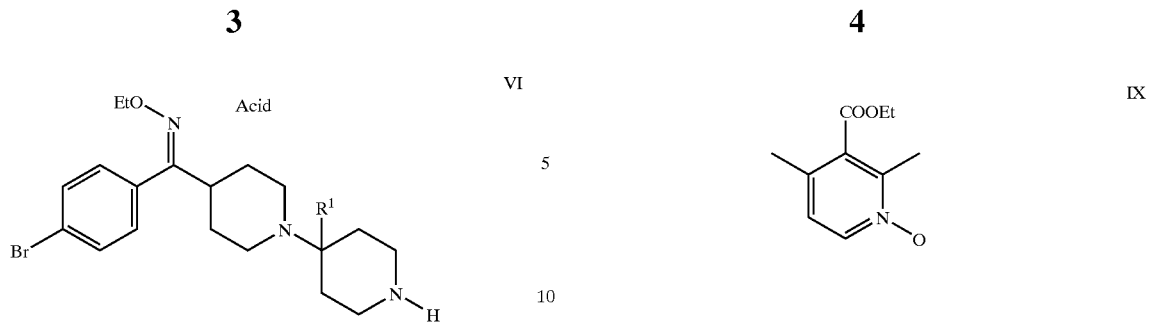

and (e) reacting said compound of formula VI with a compound of formula VII:

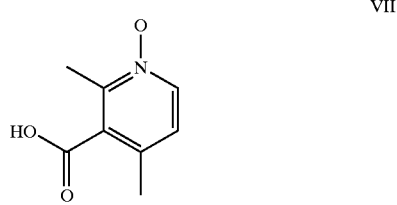

to yield the compound of formula I (when $R^1$ is methyl).

The compound of formula VII is separately prepared from a compound of formula VIII:

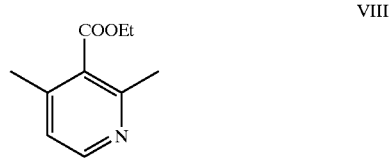

by a process comprising first oxidizing the compound of formula VIII to a compound of formula IX:

followed by converting the compound of formula IX to the compound of formula VII.

The inventive process to make the compound of formula I has several advantages: it is economical, can be easily scaled-up and has flexibility with respect to varying the amide moiety on the right hand side. Thus, since the amide moiety is formed during the last steps of the process, by varying the reagent carboxylic acid VII, differently structured amides may be produced with relative ease.

DESCRIPTION OF THE INVENTION

In one embodiment, the present invention discloses a novel, easy-to-use process for preparing the compound of formula I, which may later be converted to the compound of formula X, if so desired. The inventive process is schematically described in Scheme I:

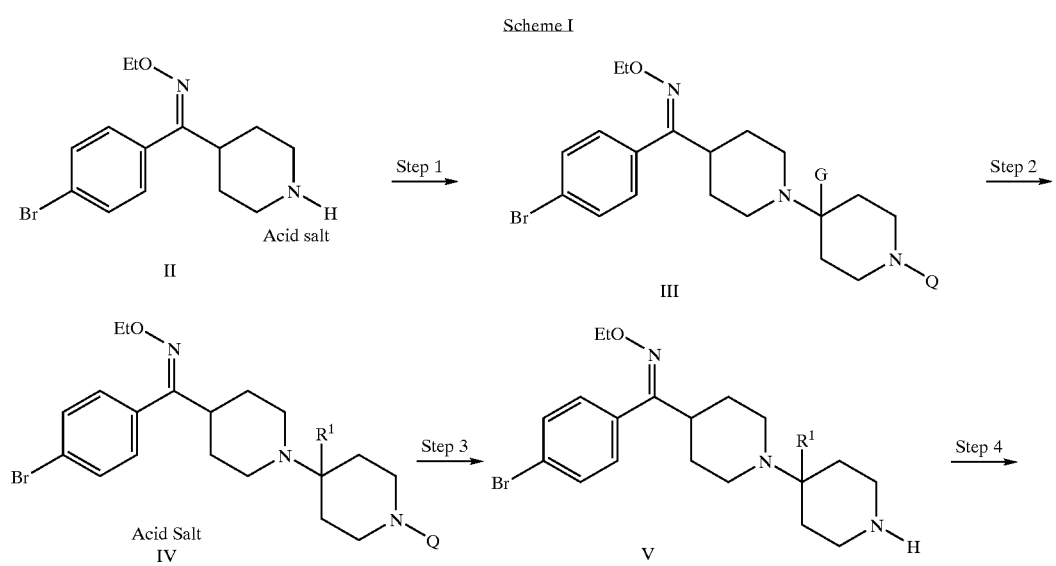

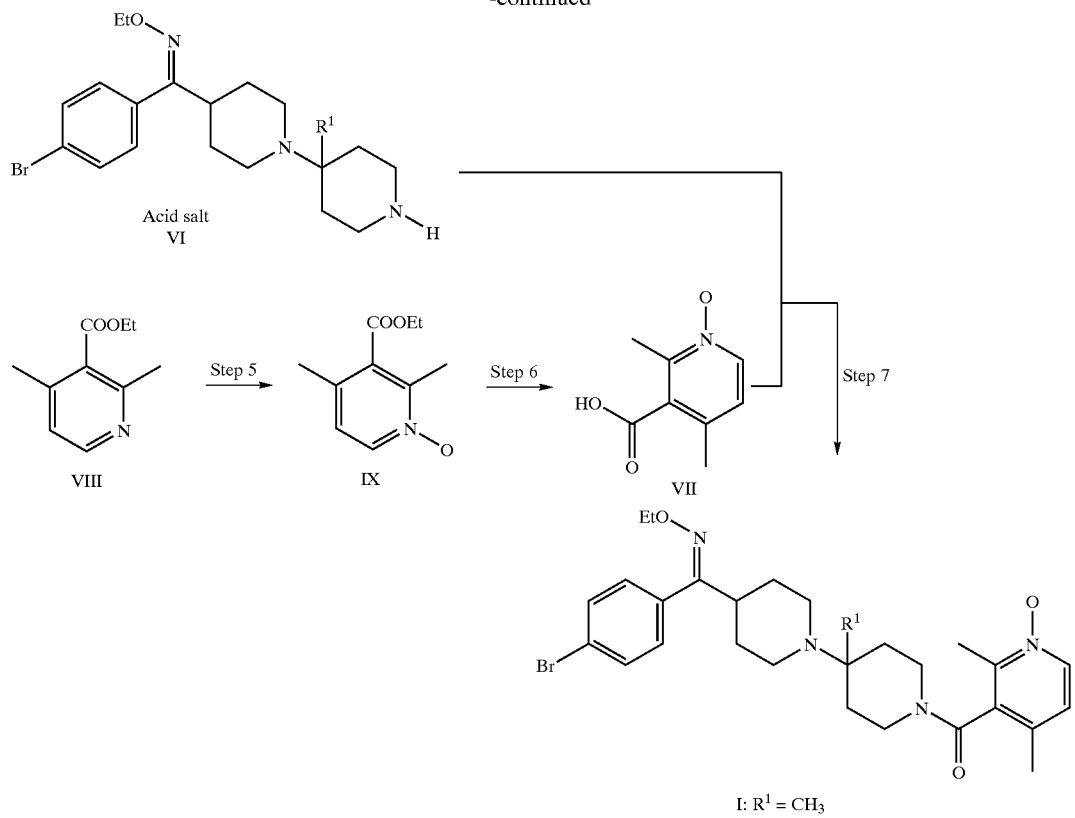

I: R¹ = CH₃

The moieties G and R¹ are defined above. Q is an N-protecting group. Examples of N-protecting groups suitable in the practice of the invention include allyl, methoxymethyl, benzyloxymethyl, CY₃CO (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, and the moiety:

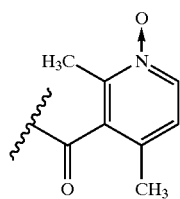

Unless otherwise defined, the term "alkyl" refers to a monovalent group derived from a straight or branched chain saturated hydrocarbon by the removal of a single atom having from 1 to 8 carbon atoms, preferably from 1 to 6. The term "aryl" represents a carbocyclic group having from 6 to 14 carbon atoms and having at least one benzenoid ring, with all available substitutable aromatic carbon atoms of the carbocyclic group being intended as possible points of attachment. Preferred aryl groups include phenyl, 1-naphthyl and 2-naphthyl, and especially phenyl. The term "halogen" represents fluorine, chlorine, bromine and iodine.

While the preferred reagents and reaction conditions for the various steps are described in detail in the Examples section, the following summarizes the details.

The process starts with the oxime compound of formula II, the synthesis of which is disclosed in pending U.S. patent application Ser. No. 60/329,562, filed of even date herewith. In step 1 in Scheme I, the compound of formula II is dissolved, suspended or dispersed in a suitable solvent such as, for example, ketone, ester, ether, hydrocarbon and the like, and mixtures thereof. Examples of suitable solvents include tetrahydrofuran, ethyl acetate, methyl ethyl ketone, dichloromethane and the like. Preferred solvent is ethyl acetate.

The compound of formula II is first converted to the free base by use of an appropriate basic compound such as, for example, a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; or a metal salt of a $C_1$–$C_{12}$ alkanol, a $C_3$–$C_{12}$ cycloalkanol, a ($C_3$–$C_8$ cycloalkyl)$C_1$–$C_6$ alkanol, ammonia, a $C_1$–$C_{12}$ alkylamine, a di($C_1$–$C_{12}$ alkyl)amine, a $C_3$–$C_8$ cycloalkylamine, a N-($C_3$–$C_8$ cycloalkyl)-N-($C_1$–$C_{12}$ alkyl) amine, a di($C_3$–$C_8$ cycloalkyl)amine, a ($C_3$–$C_8$ cycloalkyl)$C_1$–$C_6$ alkylamine, a N-($C_3$–$C_8$-cycloalkyl)$C_1$–$C_6$-alkyl-N-($C_1$–$C_{12}$ alkyl)amine, a N-($C_3$–$C_8$ cycloalkyl)$C_1$–$C_6$ alkyl-N-($C_3$–$C_8$ cycloalkyl)amine, a di[($C_1$–$C_6$ cycloalkyl)$C_1$–$C_6$ alkyl]amine and a heterocyclic amine selected from the group consisting of imidazole, triazole, pyrrolidine, piperidine, heptamethyleneimine, morpholine, thiomorpholine and a 1-($C_1$–$C_4$ alkyl)piperazine. Preferred basic compounds are KOH, NaOH, $Na_2CO_3$, $K_2CO_3$, $K_2CO_3$, $NaHCO_3$, $KHCO_3$, tetramethylguanidine, DBU, diisopropylethylamine and mixtures thereof. A preferred basic compound is a carbonate such as $Na_2CO_3$ or $K_2CO_3$, the latter being more preferred.

The free base is then converted to the compound of formula III by reacting with an appropriate reagent (suitable to introduce the G group) and an N-protected-4-piperidone. Examples of suitable reagents to introduce the G group include HCN, acetone cyanohydrin; cyclohexanone cyanohydrin; a mixture of $(C_2H_5)_2AlCN$ and $Ti(OPr)_4$, a mixture of acetic acid, $H_2SO_4$; $NaHSO_4$, $KHSO_3$ or $Na_2S_2O_5$ and a cyanide source such as NaCN or KCN;; trimethylsilylcyanide; glycolonitrile; mandelonitrile; glycinonitrile; acetone amino nitrile; and dimethylaminoacetonitrile; phenol, thiophenol, methanesulfonic acid, toluenesulfonic acid, acetic acid, trifluoroacetic acid and benzotriazole. Preferred leaving group is CN which may be introduced by use of an appropriate cyanating agent selected from the list above. Preferred cyanating agent is acetone cyanohydrin.

Examples of Q, the N-protecting group, are listed above. Preferred N-protecting group is the t-Boc (or "Boc" for short) group, especially with cyano as the leaving group G. In a general process to prepare the compound of formula III with such substitutions, the free base in the solvent is mixed with the N-Boc piperidone (e.g., N-Boc piperidin-4-one) and the cyanating agent and heated to an elevated temperature, generally the reflux temperature, for about 1–5 hours. The N-Boc piperdone is used generally in about 0.5 to 4 molar equivalents with respect to the compound of formula II, preferably in about 0.8 to about 2 molar equivalents and typically in about 1–1.5 molar equivalents. The cyanating compound is used generally in about 0.2 to about 5 molar equivalents with respect to the compound of formula II, preferably in about 0.5 to about 3.5 molar equivalents and typically in about 1 to about 2 molar equivalents. The formed product III may be isolated or used directly in the subsequent reaction step 2.

Reaction step 2 is a Grignard addition reaction. Generally, the ester solvent is removed from the last step and replaced by a hydrocarbon solvent such as, for example, toluene, xylene, chlorobenzene, dichlorobenzene and the like, or mixture of a hydrocarbon listed above with an ether such as, for example, a $C_5$–$C_{12}$ alkyl ether, 1,2-dimethoxyethane, 1.2-diethoxyethane, diglyme, 1,4-dioxane, tetrahydrofuran and the like. The solution is cooled to around −10° C. to about 10° C. and slowly treated with a Grignard reagent such as, for example, MeMgCl, MeMgBr and MeMgI, preferably MeMgCl, for about 10–120 minutes, then warmed to about 25–50° C. and kept thereat for about 2–10 hours. The Grignard reagent is used generally in about 1–4 molar equivalents with respect to the compound of formula III, preferably in about 1–3 molar equivalents and typically in about 1.5–2.5 molar equivalents. The product of formula IV may be isolated by customary work-up procedures, such as, for example, treatment with an acid (e.g. HCl) in a solvent (e.g., ethyl acetate).

Step 3 is a hydrolysis where the N-Boc protecting group is cleaved, which may be accomplished by well known procedures. An example would be acid hydrolysis, where the compound of formula IV is treated with an acid such as, for example, trifluoroacetic acid and the like, preferably in an organic solvent such as, for example, toluene, xylene, chlorobenzene, dichlorobenzene and the like, at temperatures ranging from ambient to about −5° C. to about 20° C. The product may be extracted into the organic solvent and isolated by procedures well known to those skilled in the art. The product of formula V may be converted it into an acid salt of formula VI such as oxalate, tartarate, citrate and the like by reacting with the appropriate acid (e.g., oxalic acid, tartaric acid and citric acid) in step 4.

Compound IX may be prepared from compound VIII in step 5 by known N-oxidation procedures. Generally, a peroxide such as $H_2O_2$ or an inorganic or organic peroxide, or complexes and adducts containing such peroxides or peroxy compounds, peracids, other oxidizing agents and the like may be used. Examples of suitable oxidizing agents include m-chloroperbenzoic acid; phthalic anhydride/urea-$H_2O_2$; $KMnO4$; oxone; ozone; inorganic peracids; peracetic acid; $Na_2WO_4$; a mixture of benzonitrile, $H_2O_2$ and methanol; a mixture of trifluoroacetic acid, $H_2O_2$ and $H_2SO_4$ and the like. In a general procedure, a mixture of a compound such as phthalic anhydride, urea-$H_2O_2$ and the compound of formula VIII may be dissolved, or dispersed or suspended in an appropriate solvent such as, for example, a $C_3$–$C_9$ alkanone, a $C_4$–$C_{10}$ cycloalkanone, a $C_5$–$C_{12}$ alkyl ether, 1,2-dimethoxyethane, 1,2-diethoxyethane, acetonitrile, benzonitrile, diglyme, tetrahydrofuran, 1,4-dioxan, benzene, toluene, xylene, chlorobenzene, dichlorobenzene, acetonitrile, dimethyl sulphoxide, sulpholane and the like and mixtures thereof, preferably a ketone such as methyl ethyl ketone or a nitrile such as acetonitrile, and more preferably acetonitrile, and maintained at a temperature between 0 and 50° C. for about 30 minutes to about 5 hours to complete the reaction. The phthalic anhydride may be used generally in about 1–5 molar equivalents, preferably in about 1–3 molar equivalents and typically in about 1–2 molar equivalents, with respect to the compound of formula VIII. The urea-hydrogen peroxide is generally used in about 1–8 molar equivalents, preferably in about 1–4 molar equivalents and typically in about 1–3 molar equivalents. The product of formula IX may be isolated by customary procedures well known to those skilled in the art.

Compound of formula IX may be converted to a compound of formula VII by appropriate hydrolysis method in step 6. Preferably base hydrolysis is employed. Useful bases are, for example, a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc cadmium, mercury and cerium; or a metal salt of a $C_1$–$C_{12}$ alkanol, a $C_3$–$C_{12}$ cycloalkanol, a ($C_3$–$C_8$ cycloalkyl)$C_1$–$C_6$ alkanol and the like, preferably a metal hydroxide, and more preferably KOH, NaOH, LiOH and CsOH. A solvent may be used additionally. Water is generally used as a cosolvent. Useful solvents are, for example, ether, alcohol, nitrile, hydrocarbon, ester, ketone and the like, such as, a $C_1$–$C_{12}$ alkanol, a $C_3$–$C_{12}$ cycloalkanol, a ($C_3$–$C_8$ cycloalkyl)$C_1$–$C_6$ alkanol, a $C_3$–$C_9$ alkanone, a $C_4$–$C_{10}$ cycloalkanone, a $C_5$–$C_{12}$ alkyl ether, 1,2-dimethoxyethane, 1,2-diethoxyethane, diglyme, tetrahydrofuran, 1,4-dioxan, benzene, toluene, xylene, chlorobenzene, dichlorobenzene, acetonitrile, dimethyl sulphoxide, sulpholane and the like and mixtures thereof. Preferred solvents are alcohol, ether, nitrile and the like such as, for example, ethanol, THF, acetonitrile and the like and mixtures thereof. The base is used generally in about 1–10 molar equivalents with respect to the compound of formula IX, preferably in about 1–5 molar equivalents and typically in about 1–2 molar equivalents. Generally, the compound of formula IX may be mixed with the solvent and the base and reacted at a temperature range of ambient to about 70° C., and the carboxylic acid of formula VII may be isolated by processes well known to those skilled in the art.

The compounds of formula VI and VII may be reacted in step 7 to form the desired compound of formula I as follows. The free base is liberated, preferably in situ from compound VI by use of a base such as for example, a metal hydroxide, metal carbonate and metal bicarbonate such as, for example, KOH, LiOH, NaHCO$_3$, K$_2$CO$_3$, NaHCO$_3$, and the like, generally in an organic solvent in the presence of water. Suitable solvents are, for example, THF and similar ethers, acetonitrile, methyl ethyl ketone and the like. The compound of formula VII may be added, along with a suitable coupling agent and a solvent such as, for example, a hydrocarbon, ether, alcohol, ketone, nitrile, ester and mixtures thereof, at about 40–100° C. for about 1–5 hours. Suitable coupling agents are, for example, ethyl chloroformate; isobutyl chloroformate; methanesulfonyl chloride; toluenesulfonyl chloride; diethyl chlorophosphonate; diethyl cyanophosphite; 1,1-carbonyldiimidazole; N,N-dicyclohexylcarbodiimide (DCC); (7-azabenzotriazol-1-yl)oxytris(dimethylamonino) phosphonium hexafluorophosphate ("AOP"); benzotriazol-1-yloxytris(diemthylamino)phosphonium hexafluorophosphate ("BOP"); bis(2-oxo-3-oxazolidinyl)phosphinic chloride ("BOP-Cl"); bromotris(dimethylamino) phosphonium hexafluorophosphate ("BroP"); bis (tetramethylenefluoroformamidinium)hexaflurophosphate ("BTFFH"); 2-chloro-1,3-dimethylimidazolidinium hexafluorophosphate ("CIP"); diphenylphosphinic chloride ("DppCl"); O-(7-azabenzotriazol-1-yl)-1,3-dimethyl-1,3-trimethyleneuronium hexafluorophosphate ("HAMTU"); O-(7-azabenzotriazol-1-yl)1,1,3,3-bis(tetramethyelne) uronium hexafluorophosphate ("HAPipU"); S-(7-azabenzotriazol-1-yl)-1,1,3,3-bis(tetramethylene) thiouronium hexafluorophosphate ("HAPyTU"); O-(7-azabenzotriazol-1yl)1,1,3,3-bis(tetramethylene)uronium hexafluorophosphate ("HAPyU"); O-(7-azabenzotriazol-1-yl)-1,1,3,3-tetramethyluronium hexafluorophosphate ("HATU"); O-(benzotriazol-1-yl)-1,1,3,3-bis (pentamethylene)uronium hexafluorophosphate ("HBPipU"); O-(benzotriazol-1-yl)-1,1,3,3(tetramethylene) uronium hexafluorophosphate ("HBPyU"); O-(benzotriazolyl-1-yl)-1,1,3,3-tetramethyluronium hexafluorophosphate ("HBTU"); S-(1-Oxido-2-pyridinyl)-1,1,3,3-tetramethylthiouronium hexafluorophosphate ("HOTT"); (7-azabenzotriazol-1-yl-)oxytris(pyrrolidino) phosphonium hexafluorophosphate ("PyAOP"); benzotriazol-1-yloxy-tripyrrolidinophosphonium hexafluorophosphate ("PyBOP"); bromotripyrrolidinophosphonium hexafluorophosphate ("PyBrOP"); chlorotripyrrolidinophosphonium hexafluorophosphate ("PyCIOP"); chloro-1,1,3,3-bis(tetramethylene)formamidinium hexafluorophosphate ("PyCIU"); propanephosphoric anhydride ("PPA"); O-(benzotriazol-1-yl)-1,1,3,3-tetramethyluronium tetrafluoroborate ("TBTU"); O-(3,4-dihydro-4-oxo-1,2,3-benzotriazin-3-yl)1,1,3,3-tetramethyluronium tetrafluoroborate ("TDBTU"); tetramethylfluoroformamidinium hexafluorophosphate ("TFFH"); S-(1-oxido-2-pyrodinyl)-1,1,3,3-tetramethylthiouronium hexafluorophosphate ("TOTT"); and 1-ethyl-3-(3-dimethylaminopropyl)-carbodiimide ("EDCI") hydrochloride salt with or without 1-hydroxybenzotriazole hydrate ("HOBT"), with the preferred being EDCI hydrochloride, especially in combination with HOBT. The EDCI hydrochloride is used generally in about 0.5 to about 4 molar equivalents with respect to the compound of formula VI, preferably in about 0.8 to about 3 molar equivalents and typically in about 1–1.5 molar equivalents. HOBT may be used generally in about 0.1 to about 2 molar equivalents, preferably in about 0.1 to about 1 molar equivalents and typically in about 0.2 to about 0.5 molar equivalents. Preferred solvents are ethanol, t-butanol, t-amyl alcohol, 1-methylcyclohexanol, tetrahydrofuran, 1,4-dioxane and the like and mixtures thereof. The amide product of formula I may be isolated by procedures well known to those skilled in the art or preferably as described in the EXAMPLES section.

If desired, the compound of formula I may be further converted to the CCR5 antagonist of formula X by suitable procedures known to those skilled in the art.

The products of the various steps in the reaction schemes described herein may be isolated and purified by conventional techniques such as, for example, filtration, recrystallization, solvent extraction, distillation, precipitation, sublimation and the like, well known to those skilled in the art. The products may be analyzed and/or checked for purity by conventional methods well known to those skilled in the art such as, for example, thin layer chromatography, NMR, HPLC, melting point, mass spectral analysis, elemental analysis and the like.

The following nonlimiting EXAMPLES are provided in order to further illustrate the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations have the stated meanings in the Examples below:

HPLC=High Performance Liquid Chromatography

M.pt: melting point

NMR=nuclear magnetic resonance spectroscopy

DMSO=dimethylsulfoxide mL=milliliters g=grams rt=room temperature (ambient)

Boc (or t-Boc)=tert-butoxycarbonyl

Example 1

Preparation of Compound of Formula III from a Compound of Formula II

Useful references are: (i) K. Sindelar et al, *Collect. Czech. Chem. Commun.*, 60 (1995), 894; (ii) E. Codere et al, *Eur. J. Med. Chem.*, 30 (1995), 463; and (iii) K. Mlinaric et al, *Organic Preparations and Procedures*, 24 (5) (1992), 501.

The oxime of formula II (10.0 g, 28.8 mmol) was suspended in ethyl acetate (100 mL) and free-based with a solution of 15% aqueous potassium carbonate (30 mL). The organic layer containing the free base was washed with water (30 mL). The organic solution was added to N-Boc piperidone (6.3 g, 32 mmol). Acetone cyanohydrin (1.8 mL, 20 mmol) was added and the solution was warmed to reflux. The reaction mixture was distilled to 50 mL over 2 hours. Additional acetone cyanohydrin (2.2 mL, 24 mmol) in ethyl acetate (100 mL) was added and the reaction mixture was concentrated to a volume of about 30 mL. Ethyl acetate that was saturated with water (60 mL) was added and the reaction was further distillated. The reaction was azeotropically dried and the reaction solvent replaced by toluene (20 mL), which was then directly used in the next step.

Example 2
Preparation of the Compound of Formula IV from the Compound of Formula III The toluene solution from Example 1 was diluted with tetrahydrofuran (50 mL), cooled to 0° C., and slowly treated with 3.0 M methyl magnesium chloride in THF (18.5 mL, 55.5 mmol) while maintaining the temperature about 0° C. The reaction mixture was stirred for 30 minutes at 0° C., then 8 hours at 40° C. and then cooled to 25° C. for quenching with 25% aqueous sodium citrate (60 mL). The organic phase washed with water and the combined organic layers were concentrated under vacuum to a volume of about 30 mL. The tetrahydrofuran in the organic layer was displaced by toluene via distillation. The resulting solution was cooled to 5° C., diluted with ethyl acetate (150 mL) and treated with 2.0M HCl in ethyl acetate (12.0 mL, 24.0 mmol). The resulting white slurry was agitated for 30 minutes at 5° C., filtered and washed with ice-cold ethyl acetate (20 mL). The product was dried to afford 11.4 g of the compound of formula IV. $^1$H NMR (400 MHz, CD$_3$OD) δ 7.6 (d, J=8.4 Hz, 2H), 7.3 (d, J=8.4 Hz, 2H), 4.1 (br, 4H), 3.7 (br, 2H), 3.1 (br, unresolved, m, 5H), 2.2 (m, 2H), 2.1 and 1.9 (br, unresolved, m, 6H), 1.5 (s, 12H); 1.2 (br, 3H), $^{13}$C NMR (400 MHz, CD$_3$OD): d 156.9, 154.9, 132.7, 132.6, 132.5, 132.4, 131.0, 130.8, 129.4, 122.3, 80.5, 71.1, 69.7, 68.3, 64.934.5, 33.2, 31.9, 29.7, 28.4, 27.2, 25.9, 16.0, 14.7, 13.5, 12.3; M. Pt: 223.1° C.; MS. Calcd for C$_{29}$H$_{38}$BrN$_3$O$_3$ 508, found 508.

Example 3
Preparation of the Compound of Formula V from the Compound of Formula IV To a suspension of 100 g (1 eq) of the compound of formula IV in 900 mL toluene at 50 to 60° C. was added 35 mL (1.5 eq) of 25% sodium hydroxide and 100 mL water at 50 to 60° C. The mixture was stirred until the solid was completely dissolved. The lower water layer was removed at 50 to 60° C. The upper organic layer was washed twice with 200 mL of water at 50 to 60° C. The organic layer was concentrated to about 400 mL at less than 50° C. under vacuum. The solution was cooled to 20 to 25° C. and the water content was ascertained to be below 0.03%. This solution was then slowly added to a mixture of 141 mL (10 eq) of trifluoroacetic acid and 100 mL toluene while maintaining the temperature below 5° C. The reaction mixture was stirred for 6 hours at 0 to 5° C. (during which time the amount of unreacted starting material was less than 3%). The reaction mixture was then added to a pre-cooled mixture of 200 mL of water and 242 mL of 25% sodium hydroxide while maintaining the temperature below 35° C. The water layer was removed at 30 to 40° C., and the organic layer was washed twice with 300 mL of water. The toluene solution, containing the compound of formula V, was concentrated to about 100 mL at less than 40° C. under vacuum. It was used directly for the next step. The compound, however, was also isolated separately for analysis. $^1$H NMR (400 MHz, DMSO-d$_6$): δ 0.81 (s, 3H), 1.11 (t, 3H), 1.29 (m, 2H), 1.37 (t, 2H), 1.55 (br., 2H), 1.68 (d, 2H), 1.99 (t, 2H), 2.45 (m, 2H), 2.75 (t, 2H), 2.90 (d, 2H), 3.33 (b, 2H), 3.96 (q, 2H), 7.2 (d, 2H), 7.6 (d, 2H).

Example 4
Preparation of the Compound of Formula VI

The toluene concentrate was diluted with 560 mL of ethanol (2B) and 160 mL of water. The resulting solution was heated to 60 to 70° C., to which was then added a solution of 51 g (2.2 eq) of oxalic acid dihydrate in 375 ml ethanol. The resulting suspension was stirred 60 to 70° C. for 0.5 hour, and then cooled to 20 to 30° C. The suspension was filtered and the collected solid was washed with 75 ml of 10% aqueous ethanol, and then with 40 ml of ethanol. The wet solid was dried under vacuum at 50 to 60° C. for at least 12 hours to give 103 g (95%) of the compound of formula VI, m.p. 241° C. $^1$H NMR (400 MHz, DMSO-d$_6$): δ 1.03 (s, 3H), 1.12 (t, 3H), 1.40 to 2.04 (m, 8H), 2.36 (m, 2H), 2.65 (m, 2H), 2.90 (m, 2H), 3.10 (m, 2H), 3.46 (m, H), 3.98 (q, 2H), 5 (br., 3H), 7.25 (d, 2H), 7.63 (d, 2H).

Example 5
Preparation of the Compound of Formula IX

A slurry of 6.6 g of phthalic anhydride and 6.3 g of Urea Hydrogen Peroxide in 16 mL of acetonitrile was heated to dissolve. The solution of 6 g of ethyl ester of formula VIII (the CAS Registry Number for the corresponding acid: 55314-30-2) was added while the temperature was controlled to be below 40° C. After stirring at 40° C. for 3 hours, the solution was cooled to 0° C. Then, it was added into a solution of 4.2 g of Na$_2$SO$_3$ and 9.2 g of K$_2$CO$_3$ in 24 mL of H$_2$O. The aqueous solution was extracted three times with EtOAc (10 mL each time). The combined organic layer was concentrated to give the desired compound of formula IX in 95% yield as an oil. $^1$H NMR (CDCl$_3$, 400 MHz): δ 8.43 (d, J=5.3 Hz, 1H), 7.02 (d, J=5.3 Hz, 1H), 4.42 (q J=7.1 Hz, 2H), 2.51 (s, 3H), 2.32 (s, 3H), 1.44 (t, J=7.1 Hz, 3H).

Example 6
Preparation of the Compound of Formula VII

To a solution of the oil (compound of formula IX) in 45 mL of THF at 20–30° C., a slurry of 2.1 g of LiOH.H$_2$O in 39 mL of H$_2$O was added. The solution was heated to 40° C. and stirred for 2 hours. After cooling the solution to 20–30° C., the aqueous solution was extracted with 15 mL of t-butyl methyl ether ("TBME"). The separated aqueous layer was then added to 23 mL of concentrated HCl. After cooling the slurry to 0° C. for 1 hour, the solid was filtered and dried under vacuum at 60° C. to give the desired compound of formula VII (5 g) in 89% yield over two steps. $^1$H NMR (DMSO, 400 MHz): δ 8.22 (d, J=6.6 Hz, 1H), 8.00 (d, J=6.6 Hz, 1H), 2.32 (s, 3H), 2.25 (s, 3H).

Example 7
Preparation of the Compound of Formula I

To an agitated solution of 32.5 g of potassium carbonate in 163L of water at 45–55° C. was added a slurry of 32.4 g of the compound of formula VI in 163 ml of THF. After addition, the mixture was agitated at 45–55° C. for 30 minutes. After separation, the organic layer was washed with a solution of 48.8 g of sodium chloride in 163 ml of water at 45–55° C., dried via azetropically distillation to a KF of less than 1% by dosing 488 ml of THF, and transferred to a slurry of 10.1 g of the compound of formula VII, 12.7 g of EDCI hydrochloride salt, and 2.2 g of HOBT in 130 ml of THF. After transfer, 15 ml of triethylamine was added. After addition, the mixture was heated to 50–55° C. for 3 hours and concentrated to a volume of about 163 ml. After the mixture was cooled to 25–30° C., 163 ml of TBME and 163 ml of water were added. After separation, the organic layer was washed with 163 ml of water twice, dried via azetropical distillation to a KF of less than 0.2% by dosing 488 ml of TBME, and treated with 1.6 g of DARCO G-60 and 1.6 g of SUPERCEL at 40–50° C. After filtration, 195 ml of acetone was added to the filtrate. The filtrate that contained 27.5 g (89.5%) of the compound of formula I was concentrated to an oil. It was crystallized from t-butylmethylether (150 ml) to afford 23.2 g (75%) of product. $^1$H NMR (400 MHz, CDCl$_3$) δ 8.14 (d, J=6.8 Hz, 1H), 7.50 (d, J=8.1 Hz, 2H), 7.10 (m, 2H), 6.98 (d, J=6.8 Hz, 1H), 4.23–4.13 (m, 1H), 4.04 (m, 2H), 3.45–3.27 (m, 2H), 2.94 (m, 2H), 2.79 (m, 1H), 2.45 and 2.42 (2s, 3H), 2.42–2.36 (m, 1H), 2.25 and 2.21 (2s, 3H), 2.16–2.04 (m, 2H), 1.99 (m, 1H), 1.78 (m, 3H), 1.53 (m, 2H), 1.38 (m, 1H), 1.26–1.15 (m, 1H), 1.17 (m, 3H), and 0.91 (s, 3H).

What is claimed is:

1. A process for preparing a compound of formula (I)

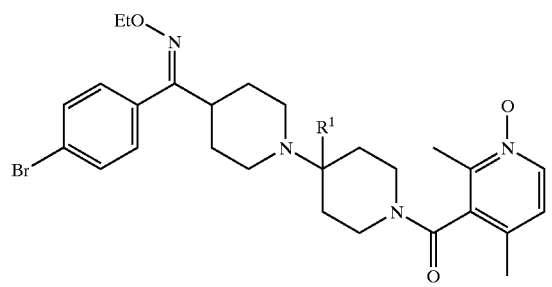

from a compound of formula II:

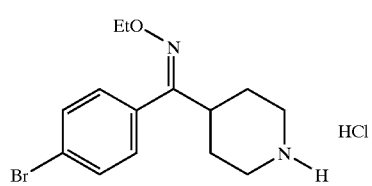

said process comprising:
(a) converting the oxime of formula II to a compound of formula III:

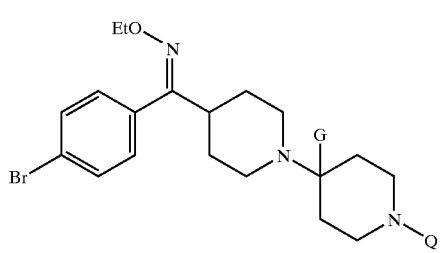

where G is a leaving group selected from the group consisting of CN, Y, OSO₂R¹, OCOCY₃ and benzotriazolyl, with R¹ being an alkyl or aryl group; Y is a halogen; and Q is an N-protecting moiety selected from the group consisting of allyl, methoxymethyl, benzyloxymethyl, CY₃CO (where Y is a halogen), benzyloxycarbonyl, trityl, pivaloyloxymethyl, tetrahydranyl, benzyl, di(p-methoxyphenyl)methyl, triphenylmethyl, (p-methoxyphenyl)diphenylmethyl, diphenylphosphinyl, benzenesulfenyl, methylcarbamate, 2-trimethylsilylethyl carbamate, 1-methyl-1-phenylethyl carbamate, t-butyl carbamate ("t-Boc"), cyclobutyl carbamate, 1-methylcyclobutyl carbamate, adamantyl carbamate, vinyl carbamate, allyl carbamate, cinnamyl carbamate, 8-quinolyl carbamate, 4,5-diphenyl-3-oxazolin-2-one, benzyl carbamate, 9-anthrylmethyl carbamate, diphenylmethyl carbamate, S-benzylcarbamate, and the moiety:

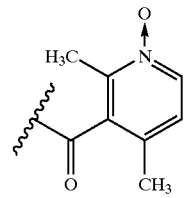

(b) reacting said compound of formula III with a suitable Grignard reagent in a suitable solvent, followed by work-up, to yield a compound of formula IV:

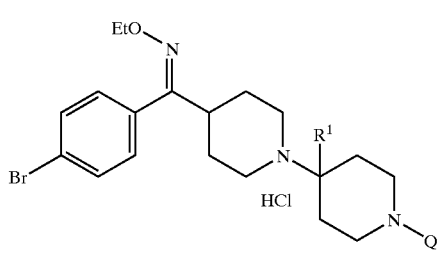

(c) deprotecting said compound of formula IV to a compound of formula V:

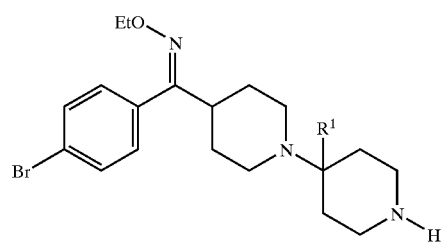

(d) forming the salt of the compound of formula V to form the compound of formula VI:

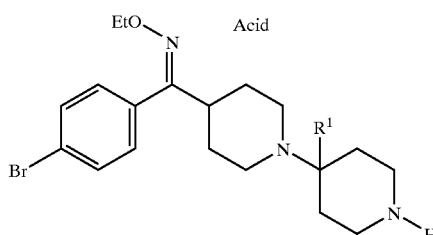

and (e) reacting said compound of formula VI with a compound of formula VII:

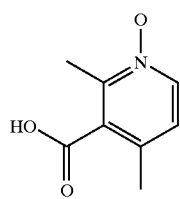

to yield the compound of formula I.

2. The process of claim 1, wherein G is CN, Q is Boc and $R^1$ is methyl.

3. The process of claim 2, wherein said compound of formula VII is prepared from a compound of formula VIII:

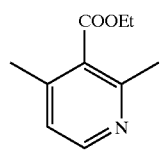

said process comprising first oxidizing the compound of formula VIII to a compound of formula IX:

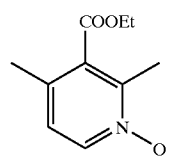

followed by converting the compound of formula IX to the compound of formula VII.

4. The process of claim 2, wherein step (a) comprises (i) converting said compound of formula II to a free base by use of a basic compound and (ii) reacting said free base with a cyanating agent and N-Boc-piperidin-4-one.

5. The process of claim 4, wherein said cyanating agent is selected from the group consisting of: HCN, acetone cyanohydrin; cyclohexanone cyanohydrin; a mixture of $(C_2H_5)_2AlCN$ and $Ti(OPr)_4$, a mixture of acetic acid, $H_2SO_4$; $NaHSO_4$, $KHSO_3$ or $Na_2S_2O_5$ and a cyanide source such as NaCN or KCN; trimethylsilylcyanide; glycolonitrile; mandelonitrile; glycinonitrile; acetone amino nitrile; and dimethylaminoacetonitrile.

6. The process of claim 5, wherein said cyanating agent is acetone cyanohydrin.

7. The process of claim 6, wherein said acetone cyanohydrin is used in about 0.2–5 molar equivalents with respect to the compound of formula II.

8. The process of claim 4, wherein said N-Boc-piperidin-4-one is used in about 0.5–4 molar equivalents with respect to the compound of formula II.

9. The process of claim 4, wherein said basic compound is selected from the group consisting of:
a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium;
a metal salt of a $C_1$–$C_{12}$ alkanol, a $C_3$–$C_{12}$ cycloalkanol, a $(C_3$–$C_8$ cycloalkyl)$C_1$–$C_6$ alkanol;
ammonia, a $C_1$–$C_{12}$ alkylamine, a di($C_1$–$C_{12}$ alkyl)amine, a $C_3$–$C_8$ cycloalkylamine, a N-($C_3$–$C_8$ cycloalkyl)-N-($C_1$–$C_{12}$ alkyl)amine. a di($C_3$–$C_8$ cycloalkyl)amine, a $(C_3$–$C_8$ cycloalkyl)$C_1$–$C_6$ alkylamine, a N-($C_3$–$C_8$-cycloalkyl)$C_1$–$C_6$-alkyl-N-($C_1$–$C_{12}$ alkyl)amine, a N-($C_3$–$C_8$ cycloalkyl)$C_1$–$C_6$ alkyl-N-($C_3$–$C_8$ cycloalkyl)amine, a di[($C_1$–$C_6$ cycloalkyl)$C_1$–$C_6$ alkyl [amine; and
a heterocyclic amine selected from the group consisting of imidazole, triazole, pyrrolidine, piperidine, heptamethyleneimine, morpholine, thiomorpholine and a 1-($C_1$–$C_4$ alkyl)piperazine.

10. The process of claim 9, wherein said basic compound is selected from the group consisting of KOH, NaOH, $Na_2CO_3$, $K_2CO_3$, $NaHCO_3$, $KHCO_3$, tetramethylguanidine, DBU, diisopropylethylamine and mixtures thereof.

11. The process of claim 10, wherein said basic compound is $Na_2CO_3$ or $K_2CO_3$.

12. The process of claim 11, wherein said basic compound is $K_2CO_3$.

13. The process of claim 2, wherein said Grignard reagent in step (b) is selected from the group consisting of MeMgCl, MeMgBr and MeMgI.

14. The process of claim 13, wherein said Grignard reagent is MeMgCl.

15. The process of claim 14, wherein said MeMgCl is used in about 1–4 molar equivalents with respect to the compound of formula III.

16. The process of claim 2, wherein said solvent in step (b) is selected from a hydrocarbon, ether, and mixtures thereof.

17. The process of claim 16, wherein said solvent is selected from toluene, xylene, chlorobenzene, or dichlorobenzene alone or in admixture with a solvent selected from the group consisting of a $C_5$–$C_{12}$ alkyl ether, 1,2-dimethoxyethane, 1.2-diethoxyethane, diglyme, 1,4-dioxane and tetrahydrofuran.

18. The process of claim 2, wherein said work-up in step (b) is treatment with an acid in an organic solvent.

19. The process of claim 18, wherein said acid is HCl and said solvent is ethyl acetate.

20. The process of claim 2, wherein said deprotection in step (c) is performed using HCl, acetic acid, trifluoroacetic acid or mixtures thereof.

21. The process of claim 20, wherein said deprotection is performed using trifluoroacetic acid.

22. The process of claim 1, wherein said salt in step (d) is an acetate, oxalate, tartarate, citrate or a benzoate.

23. The process of claim 22, wherein said salt is an oxalate.

24. The process of claim 2, wherein said reaction in step (e) is performed using a coupling agent selected from the group consisting of ethyl chloroformate; isobutyl chloroformate; methanesulfonyl chloride; toluenesulfonyl chloride; diethyl chlorophosphonate; diethyl cyanophosphite; 1,1-carbonyldiimidazole; N,N-dicyclohexylcarbodiimide; 7-azabenzotriazol-1-yl)oxytris(dimethylamonino) phosphonium hexafluorophosphate; benzotriazol-1-yloxytris(diemthylamino)phosphonium hexafluorophosphate; bis(2-oxo-3-oxazolidinyl)phosphinic chloride; bromotris(dimethylamino)phosphonium hexafluorophosphate; diphenylphosphinic chloride; propanephosphoric anhydride; bis(tetramethylenefluoroformamidinium) hexafluorophosphate; 2-chloro-1,3-dimethylimidazolidinium hexafluorophosphate; O-(7-azabenzotriazol-1-yl)-1,3-dimethyl-1,3-trimethyleneuronium hexafluorophosphate; O-(7-azabenzotriazol-1-yl)1,1,3,3-bis(tetramethylene)

uronium hexafluorophosphate; S-(7-azabenzotriazol-1-yl)-1,1,3,3-bis(tetramethylene)thiouronium hexafluorophosphate; O-(7-azabenzotriazol-1yl)1,1,3,3-bis(tetramethylene) uronium hexafluorophosphate; O-(7-azabenzotriazol-1-yl)-1,1,3,3-tetramethyluronium hexafluorophosphate; O-(benzotriazol-1-yl)-1,1,3,3-bis(pentamethylene)uronium hexafluorophosphate; O-(benzotriazol-1-yl)-1,1,3,3 (tetramethylene)uronium hexafluorophosphate; O-(benzotriazolyl-1-yl)-1,1,3,3-tetramethyluronium hexafluorophosphate; S-(1-Oxido-2-pyridinyl)-1,1,3,3-tetramethylthiouronium hexafluorophosphate; (7-azabenzotriazol-1-yl-)oxytris(pyrrolidino)phosphonium hexafluorophosphate; benzotriazol-1-yloxy-tripyrrolidinophosphonium hexafluorophosphate; bromotripyrrolidinophosphonium hexafluorophosphate; chlorotripyrrolidinophosphonium hexafluorophosphate; chloro-1,1,3,3-bis(tetramethylene)formamidinium hexafluorophosphate; O-(benzotriazol-1-yl)-1,1,3,3-tetramethyluronium tetrafluoroborate; O-(3,4-dihydro-4-oxo-1,2,3-benzotriazin-3-yl)1,1,3,3-tetramethyluronium tetrafluoroborate; tetramethylfluoroformamidinium hexafluorophosphate; S-(1-oxido-2-pyrodinyl)-1,1,3,3-tetramethylthiouronium hexafluorophosphate; and 1-ethyl-3-(3-dimethylaminopropyl)-carbodiimide hydrochloride salt with or without 1-hydroxybenzotriazole hydrate.

25. The process of claim 24, wherein said coupling agent is 1-ethyl-3-(3-dimethylaminopropyl)-carbodiimide hydrochloride salt with 1-hydroxybenzotriazole hydrate, in the presence of a solvent.

26. The process of claim 25, wherein said solvent is selected from the group consisting of a hydrocarbon, ether, alcohol, ketone, ester and mixtures thereof.

27. The process of claim 26, wherein said solvent is selected from the group consisting of ethanol, t-butanol, t-amyl alcohol, 1-methylcyclohexanol, tetrahydrofuran, 1,4-dioxane and mixtures thereof.

28. The process of claim 27, wherein said solvent is a mixture of an alcohol and an ether.

29. The process of claim 28, wherein said alcohol is butanol and said ether is THF.

30. The process of claim 29, wherein said 1-ethyl-3-(3-dimethylaminopropyl)-carbodiimide hydrochloride salt is used in about 0.5 to about 4 molar equivalents, and said 1-hydroxybenzotriazole hydrate is used in about 0.1 to about 2 molar equivalents, both with respect to the compound of formula VI.

31. The process of claim 3, wherein said oxidation of the compound of formula VIII is performed using a reagent selected from the group consisting of $H_2O_2$; inorganic peroxide; organic peroxide; peroxide-containing complexes; inorganic peroxide; inorganic oxidizing reagent; peracid; peracid-generating complex; and a peroxy compound, in a solvent.

32. The process of claim 31, wherein said reagent is m-chloroperbenzoic acid; a combination of phthalic anhydride and urea-$H_2O_2$; KMnO4; oxone; ozone; inorganic peracids; peracetic acid; $Na_2WO_4$; a mixture of benzonitrile, $H_2O_2$ and methanol; or a mixture of trifluoroacetic acid, $H_2O_2$ and $H_2SO_4$.

33. The process of claim 32, wherein said reagent is the combination of phthalic anhydride and urea-$H_2O_2$.

34. The process of claim 31, wherein said solvent is selected from the group consisting of a $C_3$–$C_9$ alkanone, a $C_4$–$C_{10}$ cycloalkanone, a $C_5$–$C_{12}$ alkyl ether, 1,2-dimethoxyethane, 1,2-diethoxyethane, acetonitrile, benzonitrile, diglyme, tetrahydrofuran, 1,4-dioxan, benzene, toluene, xylene, chlorobenzene, dichlorobenzene, acetonitrile, dimethyl sulphoxide, sulpholane and mixtures thereof.

35. The process of claim 34, wherein said solvent is methyl ethyl ketone or acetonitrile.

36. The process of claim 35, wherein said solvent is acetonitrile.

37. The process of claim 33, wherein said phthalic anhydride is used in about 1–5 molar equivalents, and said urea/$H_2O_2$ is used in about 1–8 molar equivalents, both with respect to the compound of formula VIII.

38. The process of claim 3, wherein said conversion of the compound of formula IX to the compound of formula VII is base-catalyzed.

39. The process of claim 38, wherein said base is selected from the group consisting of a metal hydroxide, oxide, carbonate and a bicarbonate, wherein the metal is selected from the group consisting of lithium, sodium, potassium, rubidium, cesium, beryllium, magnesium, calcium, strontium, barium, aluminum, indium, thallium, titanium, zirconium, cobalt, copper, silver, zinc, cadmium, mercury and cerium; and a metal salt of a $C_1$–$C_{12}$ alkanol, a $C_3$–$C_{12}$ cycloalkanol, a ($C_3$–$C_8$ cycloalkyl)$C_1$–$C_6$ alkanol.

40. The process of claim 39, wherein said base is a metal hydroxide.

41. The process of claim 40, wherein said base is LiOH.

42. The process of claim 2, wherein said compound of formula I is further converted to an acid salt of formula X:

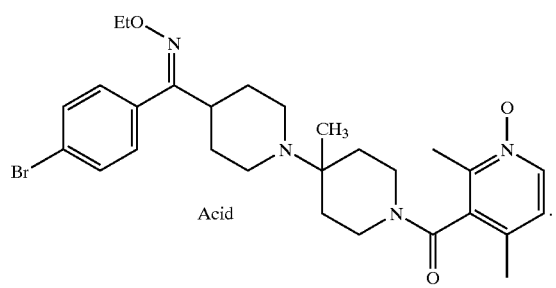

* * * * *

UNITED STATES PATENT AND TRADEMARK OFFICE
CERTIFICATE OF CORRECTION

PATENT NO.        : 6,818,773 B2
APPLICATION NO.   : 10/269822
DATED             : November 16, 2004
INVENTOR(S)       : Minzhang Chen et al.

Page 1 of 1

It is certified that error appears in the above-identified patent and that said Letters Patent is hereby corrected as shown below:

On The Title Page, Item (54)

Please correct title to read:

--Synthesis of 4-[(Z)-(4-Bromophenyl)(ethoxyimino)methyl]

-1'-[(2,4-dimethyl-1-oxido-3-pyridinyl)carbonyl]-4'-methyl-1,4'-bipiperidine--

Signed and Sealed this

Nineteenth Day of February, 2008

JON W. DUDAS
*Director of the United States Patent and Trademark Office*

UNITED STATES PATENT AND TRADEMARK OFFICE
CERTIFICATE OF CORRECTION

PATENT NO.       : 6,818,773 B2                                        Page 1 of 1
APPLICATION NO. : 10/269822
DATED            : November 16, 2004
INVENTOR(S)      : Minzhang Chen et al.

It is certified that error appears in the above-identified patent and that said Letters Patent is hereby corrected as shown below:

On The Title Page, Item (54) and Column 1, lines 1-4,

Please correct title to read:

--Synthesis of 4-[(Z)-(4-Bromophenyl)(ethoxyimino)methyl]

-1'-[(2,4-dimethyl-1-oxido-3-pyridinyl)carbonyl]-4'-methyl-1,4'-bipiperidine--

This certificate supersedes the Certificate of Correction issued February 19, 2008.

Signed and Sealed this

Eleventh Day of March, 2008

JON W. DUDAS
*Director of the United States Patent and Trademark Office*